(12) United States Patent
Yu et al.

(10) Patent No.: US 10,268,799 B2
(45) Date of Patent: Apr. 23, 2019

(54) SCREENING METHODS FOR THYROID HORMONE DISRUPTORS BASED ON CO-REGULATOR INVOLVED SIMULATIONS

(71) Applicant: Nanjing University, Nanjing, Jiangsu (CN)

(72) Inventors: Hongxia Yu, Jiangsu (CN); Wei Shi, Jiangsu (CN); Qinchang Chen, Jiangsu (CN); Xiaoxiang Wang, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 177 days.

(21) Appl. No.: 15/203,877

(22) Filed: Jul. 7, 2016

(65) Prior Publication Data

US 2017/0285007 A1    Oct. 5, 2017

(30) Foreign Application Priority Data

Apr. 1, 2016    (CN) .......................... 2016 1 0201950

(51) Int. Cl.
| | |
|---|---|
| *G01N 33/50* | (2006.01) |
| *G06F 19/12* | (2011.01) |
| *G06F 19/16* | (2011.01) |
| *G06F 19/18* | (2011.01) |

(52) U.S. Cl.
CPC .............. *G06F 19/12* (2013.01); *G06F 19/16* (2013.01); *G06F 19/18* (2013.01); *G01N 2333/723* (2013.01)

(58) Field of Classification Search
None
See application file for complete search history.

(56) References Cited

PUBLICATIONS

Koenig R. Thyroid, vol. 8, No. 8, 703-713, 1998.*
Jackson et al. Molecular Endocrinology, 11(6), 693-705.*
Pissios et al. Molecular Cell, vol. 6, 245-253, Aug. 2000.*
Zhou, T., et al., Developmental exposure to brominated diphenyl ethers results in thyroid hormone disruption. Toxicological Sciences, 2002. 66(1): p. 105-116.
Zoeller, R.T. and K.M. Crofton, Thyroid hormone action in fetal brain development and potential for disruption by environmental chemicals. Neurotoxicology, 2000. 21(6): p. 935-946.
Chen, A., et al., Hydroxylated polybrominated diphenyl ethers in paired maternal and cord sera. Environmental science & technology, 2013. 47(8): p. 3902-3908.
Kitamura, S., et al., Anti-thyroid hormonal activity of tetrabromobisphenol A, a flame retardant, and related compounds: affinity to the mammalian thyroid hormone receptor, and effect on tadpole metamorphosis. Life sciences, 2005. 76(14): p. 1589-1601.
Liu, H., et al., In vitro profiling of endocrine disrupting potency of 2, 2', 4, 4'-tetrabromodiphenyl ether (BDE47) and related hydroxylated analogs (HO-PBDEs). Marine pollution bulletin, 2011. 63(5): p. 287-296.
Ren, X.-M., et al., Hydroxylated polybrominated diphenyl ethers exhibit different activities on thyroid hormone receptors depending on their degree of bromination. Toxicology and applied pharmacology, 2013. 268(3): p. 256-263.
Li, L., et al., Non-monotonic dose—response relationship in steroid hormone receptor-mediated gene expression. Journal of molecular endocrinology, 2007. 38(5): p. 569-585.
Wang, X., et al., Effects of HO-/MeO-PBDEs on androgen receptor: in vitro investigation and helix 12-involved MD simulation. Environmental science & technology, 2013.47(20): p. 11802-11809.
Clark, R.D. and U. Norinder, Two personal perspectives on a key issue in contemporary 3D QSAR. Wiley Interdisciplinary Reviews: Computational Molecular Science, 2012.2(1): p. 108-113.
Mangoni, M., D. Roccatano, and A. Di Nola, Docking of flexible ligands to flexible receptors in solution by molecular dynamics simulation. Proteins: Structure, Function, and Bioinformatics, 1999. 35(2): p. 153-162.
Martinez, L., et al., Molecular dynamics simulations of ligand dissociation from thyroid hormone receptors: evidence of the likeliest escape pathway and its implications for the design of novel ligands. Journal of medicinal chemistry, 2006. 19(1): p. 23-26.
Glass, C.K. and M.G. Rosenfeld, The coregulator exchange in transcriptional functions of nuclear receptors. Genes & development, 2000. 14(2): p. 121-141.
Estebanez-Perpina, E., et al., Structural insight into the mode of action of a direct inhibitor of coregulator binding to the thyroid hormone receptor. Molecular Endocrinology, 2007. 21(12): p. 2919-2928.
Wen, L. and Y.-B. Shi, Unliganded thyroid hormone receptor α controls developmental timing in Xenopus tropicalis. Endocrinology, 2014.
Arnold, L.A., et al., Discovery of small molecule inhibitors of the interaction of the thyroid hormone receptor with transcriptional coregulators. Journal of Biological Chemistry, 2005. 280(52): p. 43048-43055.
Baniahmad, A., et al., The tau 4 activation domain of the thyroid hormone receptor is required for release of a putative corepressor (s) necessary for transcriptional silencing. Molecular and Cellular Biology, 1995. 15(1): p. 76-86.

(Continued)

*Primary Examiner* — Michael L Borin
(74) *Attorney, Agent, or Firm* — Rankin, Hill & Clark LLP

(57) ABSTRACT

The present patent relates to a method for qualitative identification and quantitative prediction of thyroid hormone disrupting chemicals base on the interaction between thyroid hormone receptor and co-regulators (coactivator and corepressor). The method identifies chemicals as passive antagonists, active antagonists and agonists by means of co-regulator involved molecular dynamics simulations, and predicts the relative disrupting potencies by use of binding free energy, therefore, may be used for screening of thyroid hormone disruptors among environmental pollutants. Upon more comprehensive consideration of the functioning mechanism of thyroid hormone receptor, the present invention is able to sufficiently identify thyroid hormone disruptors as agonists and antagonists, and gives more accurate prediction of the disrupting potency. Further, since nuclear receptors, just as thyroid hormone receptor, are strongly associated with co-regulators, the method may be expanded to the screening of nuclear receptor mediated endocrine disruptors.

12 Claims, 4 Drawing Sheets

(56) References Cited

PUBLICATIONS

Schoch, G.A., et al., Molecular switch in the glucocorticoid receptor: active and passive antagonist conformations. Journal of molecular biology, 2010. 395(3): p. 568-577.
Brown, S.P. and S.W. Muchmore, High-throughput calculation of protein-ligand binding affinities: modification and adaptation of the MM-PBSA protocol to enterprise grid computing. Journal of chemical information and modeling, 2006. 46(3): p. 999-1005.
Yang, Y., et al., Molecular dynamics simulation, free energy calculation and structure-based 3D-QSAR studies of B-RAF kinase inhibitors. Journal of chemical information and modeling, 2011. 51(3): p. 680-692.
Harris, J.B., et al., A computational approach predicting CYP450 metabolism and estrogenic activity of an endocrine disrupting compound (PCB-30). Environmental toxicology and chemistry, 2014. 33(7): p. 1615-1623.

* cited by examiner

SCREENING METHODS FOR THYROID HORMONE DISRUPTORS BASED ON CO-REGULATOR INVOLVED SIMULATIONS

BACKGROUND

Filed of the Invention

The present invention relates to predictive toxicology, specially a computational method for identifying and potency predicting of thyroid hormone disruptors among environmental pollutants.

Background of the Invention

Thyroid hormone (TH) plays an important role in the development, differentiation and metabolism[1]. TH disruptors have been reported to influence the development of fetal brain and central nervous system, influence the development of heart and cause various kinds of disease[2]. More and more synthetized and natural chemicals are detected in human and wildlife, and are determined to be TH disruptors, which is widely concerned[3, 4].

In order to identify potential TH disruptors, practical in vivo and in vitro assays have been developed to screen environmental pollutants[5, 6]. However, on the one hand, both in vivo and in vitro assays are extremely expensive and cost a lot of time; on the other hand, there are thousands of pollutants in the environment, which makes it impossible to screen them one by one.

Computational toxicology has been developed and virtual screen methods based on computational simulations have been accepted and developed (U.S. Pat. Nos. 9,218,460, 5,883,116), including Quantitative Structure-Activity Relationship (QSAR), molecular docking and molecular dynamics (MD) simulations[7, 8]. However, QSAR models are "ligand-based" and molecular descriptors do not integrate enough of the interactions between ligand and receptor, which has led to less precise predictions, and docking is challenged by molecular flexibility[9, 10]. Molecular dynamics (MD) simulations relax the ligand-receptor complex, and as such are recommended for more comprehensive simulations[11]. However, few MD simulations have been performed on TR and those have seldom used quantitative descriptors to make predictions.

As a member of ligand-dependent nuclear receptor (NR) superfamily, functions of TR are associated with co-regulators (coactivator and corepressor). TR contains a transactivation domain, called activation function 2 (AF-2), in the ligand binding domain (LBD), which is activated upon binding of agonists that are suitable for coactivator recruitment[12]. Binding of T3 induces a series of conformational changes of the LBD, including repositioning of helix 12 (H12), which activates AF-2 and promotes recruitment of coactivator, followed by transactivation of target genes. Corepressor binds to a surface partially overlaps AF-2 and represses relative transcription[13, 14]. It has been reported that binding of antagonists enhanced recruitment of corepressor or block binding of coactivator[15, 16]. Upon co-regulator interaction, agonists induce the binding of coactivator, while antagonists can be classified as either of two types of antagonists. A ligand is defined as a "passive antagonist" if it blocks binding of coactivator and the relative transactivation, and a ligand enhancing recruitment of corepressor is defined as an "active antagonist" [17]. Therefore, co-regulators are essential for functioning of the TR, which is essential for classification of TH disruptors. Yu, et al. (CN103324861A[P]. 2013) and Zhang, et al. (CN101381894A[P]. 2009) have estimated the endocrine disrupting effect of chemicals through the stable reposition of H12 of NRs. However, the essential co-regulators were not considered in both of these two methods, which may lead to false positive. To the best of our knowledge, no method identifying disruptors of TH have used co-regulators.

It has been a challenge to quantitatively predict relative endocrine disrupting activities. An MD study using settling time of H12 as a predictor of anti-androgenic potency has been conducted[8]. However, both stable H12 and settling time were subjectively estimated, which were not satisfactory enough for quantitative prediction. Previous studies have revealed that binding free energy can be used to predict the binding affinity and kinase inhibiting activity[18, 19]. Although binding energy was also used to compare NR-mediated endocrine disrupting activities, it was usually based on molecular docking[20]. The present method used binding free energy calculated from mechanism-based MD simulations as quantitative predictor, which makes more convincible prediction.

To our knowledge, no method was invented to identify endocrine disruptors as agonists and antagonists by use of MD simulations, nor considered co-regulators. There was no method invented to identify TH disrupting chemicals as passive antagonists, active antagonists and agonists based on the interaction with co-regulators, or to predict the relative TH disrupting potency using the mechanism-based binding free energy.

SUMMARY

The present invention relates to co-regulator involved MD simulations and binding free energy calculation for qualitative identification and quantitative prediction of TH disruptors. The reposition of H12, interaction of TR with corepressor and coactivator are used to classify disruptors as passive antagonists, active antagonists and agonists. Binding free energies calculated based on the passive antagonism, active antagonism and agonism are used for quantitative prediction of the relative TH disrupting potencies. It is the first time that the present invention adopts co-regulators in the MD simulations to identify TH disruptor according to different mechanisms, and quantitatively predicts the relative TH disrupting potencies with the help of binding free energy.

DETAILED DESCRIPTION

Technical Solutions

The present screening method for thyroid hormone disruptors based on co-regulator involved simulations can be understood by reference to the following description and the examples included therein.

Figure 1:
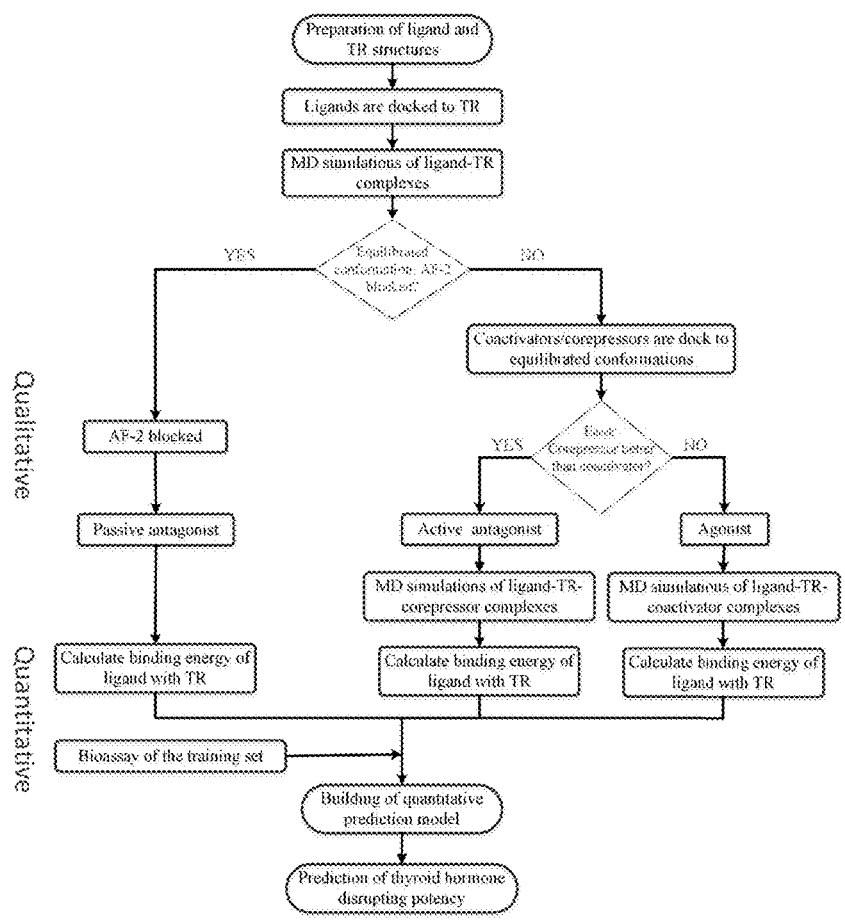
FIG. 1 depicts a protocol for prediction of thyroid hormone disrupting effect of environmental pollutants.

The protocol of the present screening method for thyroid hormone disruptors based on co-regulator involved simulations is depicted in FIG. 1, which comprises the following steps:

1) apo conformations of thyroid hormone (TH) receptor (TR) ligand binding domain (LBD) are constructed by used of the reported protein crystal as templates, followed by quality evaluation and structural optimization; ligand structures are built and optimized; the ligands are docked into the TRs to form ligand-TR complexes; Molecular dynamics (MD) simulations are performed for the ligand-TR complexes.
2) equilibrated conformations are extracted from the MD trajectories; the relative ligands are identified as passive antagonists for those helix-12s (H12s) are induced to block the coactivator binding site;
3) coactivator and corepressor are docked to the equilibrated conformations extracted in step 2) whose co-regulator binding sites are not blocked and thus be exposed to co-regulators; whether the equilibrated conformations are more attractive to coactivator or corepressor is estimated according to the docking scores; the relative ligands are identified as agonists if the equilibrated conformations are more selectively bind to coactivators; the relative ligands are identified as active antagonists if the equilibrated conformations are more selectively bind to corepressors;
4) for those identified as agonists in step 3), MD simulations are performed again for the obtained ligand-TR-coactivator complexes; for those identified as active antagonists in step 3), MD simulations are performed again for the obtained ligand-TR-corepressor complexes;
5) bioassays are performed for the representative TH disrupting chemicals to obtain the relative disrupting potencies; binding free energies with TR are calculated for the passive antagonists, active antagonists and agonists in step 2) and 4); the predicted TH disrupting potencies are calculated by the prediction models achieved by regression analysis between binding free energy and relative TH disrupting potencies.

In an embodiment of the step 1), the reported crystal structures are those can be searched and downloaded from the protein database (http://www.rcsb.org/pdb/home/home.do), which includes all published structures that are approval.

In an embodiment of the step 1), the construction of the apo conformations is based on homology modeling, the loop between H11 and H12 is constructed according to the template coded 1A52 in the protein database, the rest part is constructed based on the reported crystal structures (PDB codes: 4LNW and 1NQ0) of TRs in the protein database.

In an embodiment of the step 1), the quality of the constructed apo conformations are evaluated by Ramachandran plot.

In an embodiment of the step 1), the optimization of ligand structures is first performed with MM2 (Molecular Mechanics, Allinger Force Field version 2), followed by Powell gradient algorithm with the Tripos force field.

In an embodiment of the step 1), the MD simulations of ligand-TR complexes are performed following the protocol: CHARMM force fields are applied to the receptors and ligands, respectively; each complex is immersed with TIP3P water molecules in a box, keeping the minimum distance between the complex and the boundary larger than 1.4 nm; Na+ and Cl− ions are added to neutralize the system; all MD simulations are performed in the NPT (constant pressure and temperature) ensemble in 1 atm, 300 K, with periodic boundary conditions; electrostatic interactions are calculated with the particle mesh Ewald method, with van der Waals interactions cutoff of 1.0 nm; all simulations are performed for 20-22 ns using a 2 fs time step, and snapshots for analysis are saved every 2 ps.

In an embodiment of the step 4), the MD simulations of ligand-TR-coactivator/corepressor complexes are performed following the protocol: CHARMM force fields are applied to the receptors with coactivator/corepressor and ligands, respectively; each complex is immersed with TIP3P water molecules in a box, keeping the minimum distance between the complex and the boundary larger than 1.4 nm; Na+ and Cl− ions are added to neutralize the system; all MD simulations are performed in the NPT (constant pressure and temperature) ensemble in 1 atm, 300 K, with periodic boundary conditions; electrostatic interactions are calculated with the particle mesh Ewald method, with van der Waals interactions cutoff of 1.0 nm; all simulations are performed for 20-22 ns using a 2 fs time step, and snapshots for analysis are saved every 2 ps.

In an embodiment of the step 2), equilibrated conformations are obtained by calculation of root-mean-square deviation (RMSD) of H12, reference to backbone of the apo structures. Conformation extracted when the RMSD of H12 is equilibrated is considered equilibrated conformation.

In an embodiment of the step 2), equilibrated conformations can also be obtained by extracting conformation when H12 is in the average position of the fluctuation.

In an embodiment of the step 2), the blocking of coactivator binding site is evaluated according to the distance between H12 and key residues: for TRβ, H12 is considered blocking coactivator binding site if the distances with V284 and K306 are less than 3 Å, and the distances with K288 and I302 are less than 5 Å; for TRα, H12 is considered blocking coactivator binding site if the distances with V230 and K252 are less than 3 Å, and the distances with K234 and I248 are less than 5 Å.

In an embodiment of the step 3), docking of co-regulators to the equilibrated conformations are performed as follows:

Reference structures of receptors containing corepressor (PDB code: 2OVM) or coactivator (PDB code: 2B1V) are aligned to the extracted conformations, and the positions of co-regulators are set as the reference positions of the input co-regulators. Co-regulators were then docked to the extracted TRs using shape-based 3D fast Fourier transform (FFT) docking methods. The receptor and ligand range angles are all set to 15 degrees to make sure the co-regulators not rotate far away from the reference positions. The docking result with least $E_{dock}$(docking score) out of 500 results is chosen as the final docking result.

In an embodiment of the step 3), conformations with $E_{dock}$ of coactivator greater than corepressor are considered to selectively bind to corepressor; conformations with $E_{dock}$ of corepressor greater than coactivator are considered to selectively bind to coactivator.

In an embodiment of the step 5), binding free energy is calculated based on snapshots of every 100 ps extracted from the MD trajectories using MM-PBSA (molecular mechanics Poisson-Boltzmann surface area) method.

In an embodiment of the step 5), the binding free energies between ligands and TR used for predictions of thyroid disrupting potencies are following the rules: for prediction of passive antagonistic potencies, binding free energies are calculated by use of MD trajectories of passive antagonist-TR complexes in step 1); for prediction of active antagonistic and agonistic potencies, binding free energies are calculated by use of MD trajectories of active antagonist-TR-corepressor and agonist-TR-coactivator complexes, respectively, in step 4).

In an embodiment of the step 5), the prediction model by use of GH3 cell proliferation assay, with 11 HO-PBDEs as training set and 2 as validation set, is built and given in Equation. 1

$$-\log RIC_{20} = 0.4115 - 0.0244 \Delta G_{pas/act} \quad (1)$$

where $RIC_{20}$ (mol/L) is 20% inhibition of proliferation of GH3 cells induced by 0.5 nM T3 (triiodothyronine); $\Delta G_{pas/act}$ is the combined binding free energy combining binding free energies of TRα and TRβ with passive and active antagonists.

Beneficial Effect

In compare with previous methods, the present invention has the following significant results.

(1) The present invention considers the function of coactivator and corepressor, which are essential for the functioning of TR, in the toxicity simulations. The involvement of co-regulators gives more comprehensive consideration of the functioning mechanism of TR.

(2) The MD simulations perfectly exhibited the interaction among ligand, TR and co-regulators, which are able to effect the functioning the others.

(3) Based on the mechanism comprehension, thyroid hormone disruptors are identified and classified as passive antagonists, active antagonists and agonists, which leads to more accurate potency prediction.

(4) Agonistic and antagonistic potencies are quantitatively predicted by prediction model using binding free energy.

(5) The present invention gives more simple and sufficient prediction with less cost than in vivo and in vitro screening.

EXAMPLES

The following examples further illustrate the method of identifying TH disrupting chemicals and building of quantitative prediction model. It will be understood, however, that the examples are for better comprehension of the present invention, which should not limit what is claimed in the claim section. Many variations and modifications of the methods can be made while remaining within the scope and spirit of the present invention. For example, human and rat TRα and TRβ are used as the nuclear receptor, HO-PBDEs are used as the potential thyroid hormone disruptors in the following examples. Other nuclear receptors and other endocrine disruptors can be used for construction of virtual screen models base on the protocol.

Example 1

Apo structures of human TRα- and TRβ-LBD were built by homology modeling. Previously reported human TRα- (PDB code: 4LNX) and TRβ-LBD (PDB code: 1NQ0) were used as templates of the main bodies of TRα and TRβ, respectively, and apo structure of estrogen receptor (PDB code: 1A52) was used as the template of the loops between H11 and H12 of both receptors. Qualities of the constructed apo structures were further evaluated with Ramachandran plot generated by the Structure Analysis and Verification Server (SAVES, http://services.mbi.ucla.edu/SAVES/).

Eight HO-PBDEs with T3 are selected as ligands for this example. Ligand structures are first optimized with MM2 (Molecular Mechanics, Allinger Force Field version 2), and then optimized using Powell gradient algorithm with the Tripos force field. Then the Surflex-Dock program interfaced with SYBYL 7.3 was used to dock the optimized ligands into the docking cavities of TR-LBDs. Docking scores of the ligands were calculated and the ligand-TR complexes were used for MD simulations.

MD simulations were performed by use of GROMACS software package. The complexes were immersed with TIP3P water molecules in a box, keeping the minimum distance between the complex and the boundary larger than 1.4 nm. Na+ and Cl− ions were added to neutralize the system. All MD simulations were performed in the NPT (constant pressure and temperature) ensemble in 1 atm, 300 K, with periodic boundary conditions. Electrostatic interactions were calculated with the particle mesh Ewald method, with van der Waals interactions cutoff of 1.0 nm. All simulations were performed for 20 ns using a 2 fs time step, and snapshots for analysis are saved every 2 ps. After the MD simulations, snapshots of every 100 ps were extracted for calculation of binding free energy by use of g_mmpbsa program.

Binding affinities of ligands binding with TR were detected in the competitive binding assays, by use of Fluorescein-labeled T3 as probe. The results (FIG. 2) showed that 3 and 2 out of 8 HO-PBDEs were detected affinities binding with human TRα- and TRβ-LBD, respectively, which were much weaker than T3.

Figure 2:
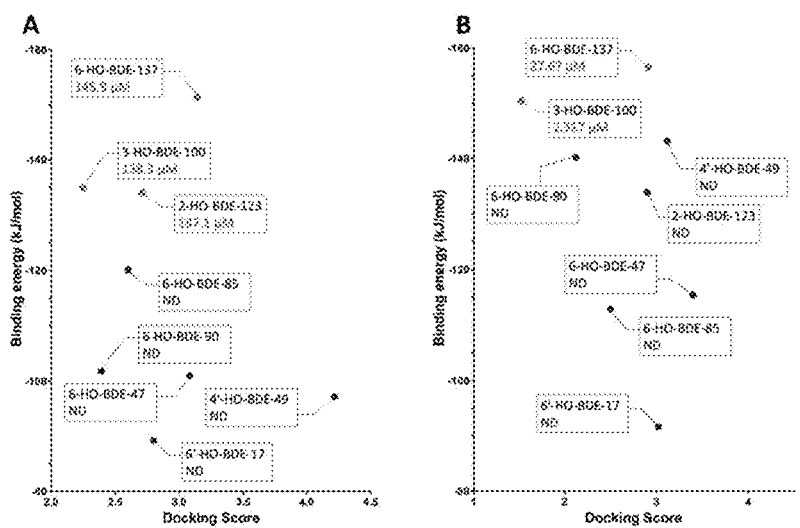
FIG. 2 depicts the comparison between binding free energy and docking score on the prediction sufficiency of binding affinity.

Lower binding free energy and higher docking score reveal greater binding affinity. However, the results of docking score and binding free energy were dramatically different (FIG. 2). The 3 HO-PBDEs (6-HO-BDE-137, 3-HO-BDE-100, 2-HO-BDE-123) with greater affinities binding with TRα in the competitive binding assays exhibited lesser binding free energy (FIG. 2A). Similar results were observed in TRβ (FIG. 2B). However, with the largest docking score among the tested HO-PBDEs, affinity of 4'-HO-BDE-49 with TRα was too weak to detect. Whereas 3-HO-BDE-100, which was predicted to be the weakest to bind TRα, was determined to be one of the strongest binding ligands (FIG. 2A). It was indicated that binding potency can be predicted by the binding free energy instead of docking scores, which established foundation to predict the relative thyroid hormone disrupting potency by use of binding free energy.

Example 2

Apo structures of rat TRα- and TRβ-LBD were constructed by homology modeling. Because no rat TR crystal structures was reported, human TRα- (PDB code: 4LNX) and TRβ-LBD (PDB code: 1NQ0) were used as templates of the main bodies of TRα and TRβ, respectively, and apo structure of estrogen receptor (PDB code: 1A52) was used as the template of the loops between H11 and H12 of both receptors. Qualities of the constructed apo structures were further evaluated with Ramachandran plot generated by the Structure Analysis and Verification Server (SAVES, http://services.mbi.ucla.edu/SAVES/).

Sixteen HO-PBDEs with T3 are selected as ligands for this example. Ligand structures are first optimized with MM2 (Molecular Mechanics, Allinger Force Field version 2), and then optimized using Powell gradient algorithm with the Tripos force field. Then the Surflex-Dock program interfaced with SYBYL 7.3 was used to dock the optimized ligands into the docking cavities of TR-LBDs. Docking scores of the ligands were calculated and the ligand-TR complexes were used for MD simulations.

MD simulations were performed by use of GROMACS software package. The complexes were immersed with TIP3P water molecules in a box, keeping the minimum distance between the complex and the boundary larger than 1.4 nm. Na+ and Cl− ions were added to neutralize the system. All MD simulations were performed in the NPT (constant pressure and temperature) ensemble in 1 atm, 300 K, with periodic boundary conditions. Electrostatic interactions were calculated with the particle mesh Ewald method, with van der Waals interactions cutoff of 1.0 nm. All simulations were performed for 20 ns using a 2 fs time step, and snapshots for analysis are saved every 2 ps.

The rat pituitary tumor cell line GH3 was cultured for determination of the relative TH disrupting potencies. Thirteen out of sixteen HO-PBDEs were determined to be thyroid hormone antagonists, with the relative anti-TH potencies (−log RIC20) ranging from 6.51 to 8.42 (Tab. 1). Due to cytotoxicity, the other 3 HO-PBDEs were not tested for anti-TH potencies.

Figure 3A:
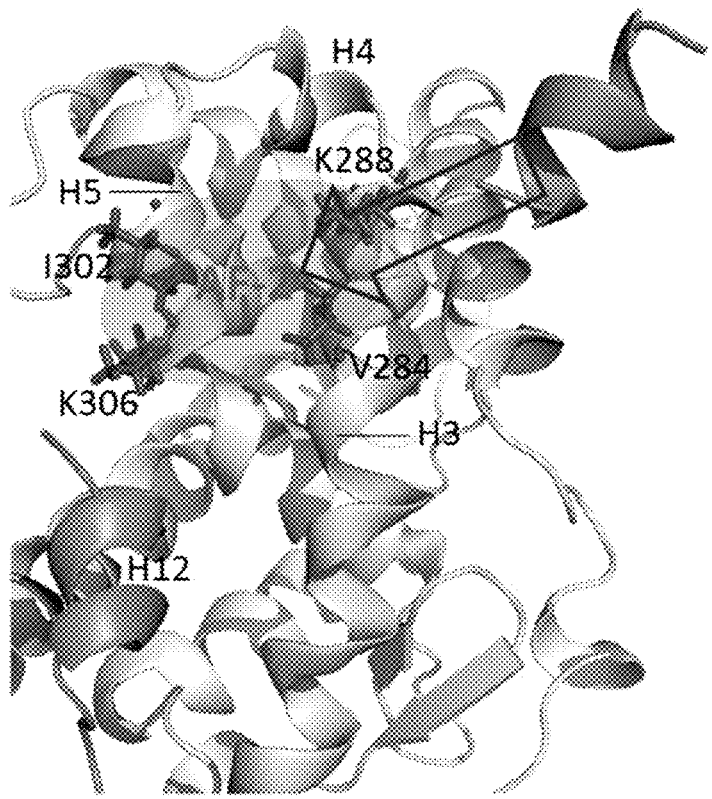
FIG. 3A depicts the conformational change of TR induced by T3 (triiodothyronine).
Figure 3B:
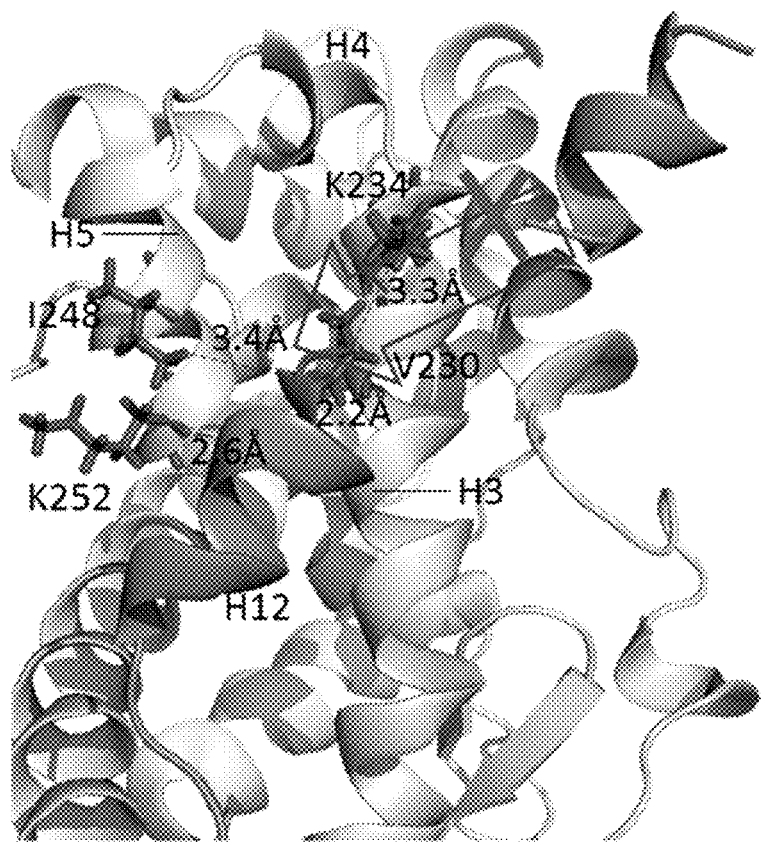
FIG. 3B depicts the conformational change of TR induced by 6-HO-BDE-85.

Snapshots of equilibrated conformations were extracted to investigate the reposition of H12 and identify chemicals as passive antagonists. For T3-bound TRβ, AF-2 was exposed to the co-regulators, so that coactivators were able to bind it (FIG. 3A). While 6-HO-BDE-85-rTRα-H12 (H12 of 6-HO-BDE-85-bound rat TRα) positioned between residues V230, K234 and I248, K252, which were components of AF-2. Distances between H12 and these residues are approximately 3 Å, and could be as close as 2.2 Å, which indicated that AF-2 was partly blocked (FIG. 3B). Blocking AF-2 prevents subsequent transactivation of the gene, thus is defined as passive antagonism. Similarly, 2-HO-BDE-123-rTRβ-H12, 4-HO-BDE-90-rTRβ-H12, and 6-HO-BDE-137-rTRβ-H12 were found to block the coactivator binding site. As a result, 6-HO-BDE-85 was identified as passive antagonist of TRα, 2-HO-BDE-123, 4-HO-BDE-90 and 6-HO-BDE-137 were identified as passive antagonists of TRβ. In this example, 2-HO-BDE-123, 4-HO-BDE-90 and 6-HO-BDE-137 were determined to be antagonists of the TR in the GH3 proliferation assay, which was consistent with the result of MD simulations.

For those co-regulator binding site was exposed to co-regulators, coactivator and corepressor were docked to the co-regulator binding site by use of Hex 8.0.0 software. Reference structures of receptors containing corepressor (PDB code: 2OVM) or coactivator (PDB code: 2B1V) are aligned to the equilibrated conformations, and the positions of co-regulators are set as the reference positions of the input co-regulators. Co-regulators were then docked to the extracted TRs using shape-based 3D fast Fourier transform (FFT) docking methods. The receptor and ligand range angles are all set to 15 degrees to make sure the co-regulators not rotate far away from the reference positions. The docking result with least $E_{dock}$ out of 500 results is chosen as the final docking result.

Figure 4A:
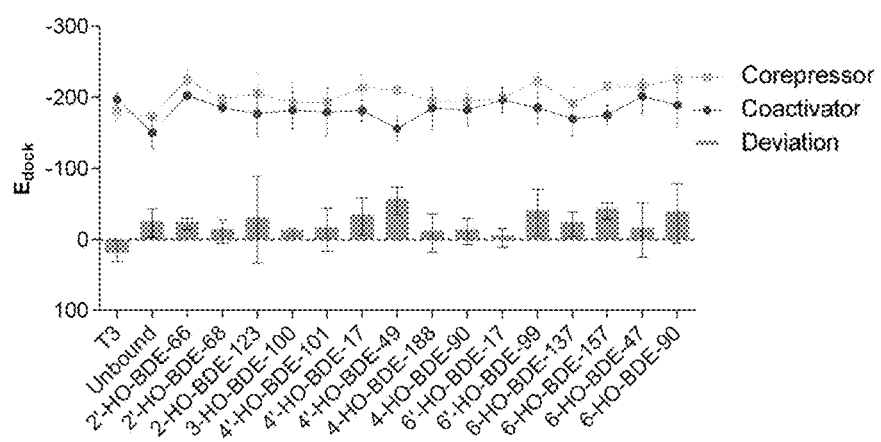
FIG. 4A depicts the protein docking results of TRα with corepressor and coactivator.
Figure 4B:
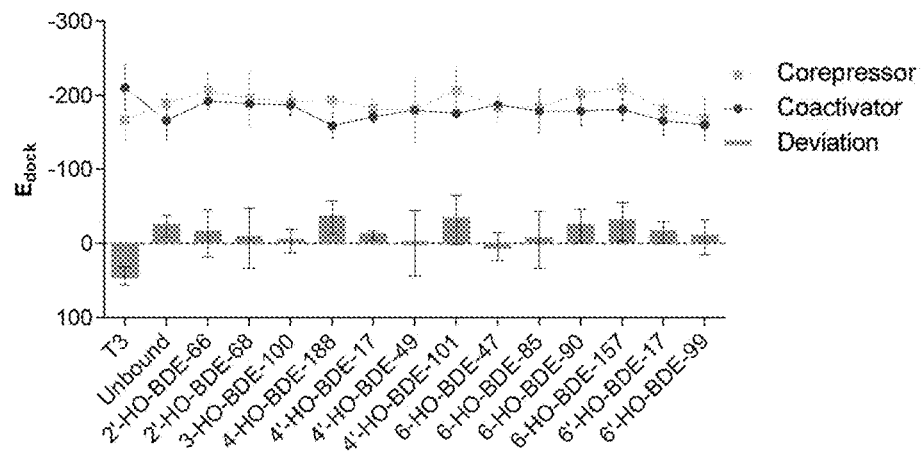
FIG. 4B depicts the protein docking results of TRβ with corepressor and coactivator.

Docking of co-regulators to TR was performed to identify chemicals as active antagonists and agonists. Most of the HO-PBDE-bound TRs bound to corepressor with $E_{dock}$ value less than that of the coactivator except 6-HO-BDE-47-bound TRβ (FIGS. 4A and 4B), which meant that corepressors were more selectively bound to them. For 2-HO-BDE-123-, 4'-HO-BDE-17-, 6-HO-BDE-157-, 6-HO-BDE-90- and 6'-HO-BDE-99-bound TRα, as well as 4-HO-BDE-188-, 4'-HO-BDE-101-, 6-HO-BDE-90- and 6-HO-BDE-157-bound TRβ, the deviation values were even less than that of unbound TRα and TRβ (about −20). Alternatively, both T3-bound TRα and TRβ bound to coactivators with $E_{dock}$ values less than that of the corepressor, which suggested that TRs bound to T3 recruit coactivators rather than corepressors. It has been reported that T3 induces recruitment of coactivators, while unbound TR is able to bind corepressors[12]. These results indicated that most of the HO-PBDEs selectively induced recruitment of corepressors rather than coactivators. Corepressor-bound TR is able to bind to relative genes and silence transactivation, which was defined as active antagonism. Therefore, HO-PBDEs causing selective binding of corepressors to TR were identified as active antagonists, while T3 was agonist of TR and 6-HO-BDE-47 was identified as agonist of TRβ.

MD simulations were performed again for the active antagonist-TR-corepressor complexes. The procedures of simulations were the same as above. Ligand-receptor binding free energies of ligand-TR complexes ($\Delta G_{lig-rTR\alpha}$ and $\Delta G_{lig-rTR\beta}$) and active antagonist-TR-corepressor complexes ($\Delta G_{lig-rTR\alpha/cor}$ and $\Delta G_{lig-rTR\beta/cor}$) were then calculated (Tab. 1). Among the thirteen HO-PBDEs that were identified as (active or passive) antagonists by MD simulations and were detected antagonists in the GH3 cell proliferation assay, two (2'-HO-BDE-66 and 4-HO-BDE-90) were selected as validation set and the other eleven were considered training set. Because the GH3 cells contain both TRα and TRβ, the binding free energies were combined before regression analysis. In this example, $\Delta G_{sum,cor-rTR}$ represented the sum of $\Delta G_{lig-rTR\alpha}$ and $\Delta G_{lig-rTR\beta}$, while $\Delta G_{pas/act}$ was the combination of $\Delta G_{lig-rTR\alpha}$ or $\Delta G_{lig-rTR\beta}$ of passive antagonist and $\Delta G_{lig-rTR\alpha/cor}$ or $\Delta G_{lig-rTR\beta/cor}$ of active antagonist.

TABLE 1

Binding free energy and the relative anti-TH potencies

| | | TRα (kJ/mol) | | TRβ (kJ/mol) | | Combined (kJ/mol) | |
|---|---|---|---|---|---|---|---|
| Ligand | −log RIC$_{20}$ | $\Delta G_{lig-rTR\alpha}$ | $\Delta G_{lig-rTR\alpha/cor}$ | $\Delta G_{lig-rTR\beta}$ | $\Delta G_{lig-rTR\beta/cor}$ | $\Delta G_{sum,\ cor-rTR}$ | $\Delta G_{pas/act}$ |
| 4-HO-BDE-188 | 8.42 | −175.2 | −170.1 | −169.7 | −169.4 | −344.9 | −339.5 |
| 3-HO-BDE-100 | 7.83 | −139.7 | −150.7 | −137.5 | −140.6 | −277.2 | −291.3 |
| 4'-HO-BDE-101 | 8.11 | −150.7 | −150.6 | −150.6 | −146.5 | −301.3 | −297.1 |
| 6-HO-BDE-157 | 8.14 | −149.5 | −150.6 | −156.8 | −154.3 | −306.3 | −304.9 |
| 6-HO-BDE-90 | 7.76 | −143.3 | −145.6 | −151.7 | −152.9 | −295.1 | −298.5 |
| 4'-HO-BDE-49 | 7.30 | −141.5 | −142.1 | −141.4 | −141.6 | −282.9 | −283.7 |
| 2'-OH-BDE-66 | 7.09 | −142.5 | −139.0 | −136.4 | −133.1 | −278.8 | −272.1 |
| 6'-HO-BDE-17 | 6.78 | −128.1 | −136.4 | −135.0 | −133.7 | −263.1 | −270.1 |
| 2'-OH-BDE-68 | 7.15 | −136.2 | −132.1 | −142.5 | −147.3 | −278.7 | −279.5 |
| 4'-OH-BDE-17 | 6.51 | −126.9 | −126.2 | −131.4 | −131.0 | −258.3 | −257.2 |
| 6-HO-BDE-137 | 8.03 | −161.3 | −156.3 | −162.2 | — | −323.5 | −318.6 |

TABLE 1-continued

Binding free energy and the relative anti-TH potencies

| Ligand | −log RIC$_{20}$ | ΔG$_{lig\text{-}rTR\alpha}$ TRα (kJ/mol) | ΔG$_{lig\text{-}rTR\alpha/cor}$ | ΔG$_{lig\text{-}rTR\beta}$ TRβ (kJ/mol) | ΔG$_{lig\text{-}rTR\beta/cor}$ | ΔG$_{sum,\ cor\text{-}rTR}$ Combined (kJ/mol) | ΔG$_{pas/act}$ |
|---|---|---|---|---|---|---|---|
| 2-HO-BDE-123 | 7.44 | −152.5 | −149.8 | −149.5 | — | −302.0 | −299.3 |
| 4-HO-BDE-90 | 7.59 | −147.8 | −151.8 | −146.2 | — | −293.9 | −297.9 |
| 6-HO-BDE-47 | — | −145.3 | −140.8 | −135.4 | — | −280.8 | — |
| 6-HO-BDE-85 | — | −138.3 | — | −150.8 | −151.3 | −289.1 | −289.6 |
| 6'-HO-BDE-99 | — | −139.1 | −137.7 | −144.3 | −148.5 | −283.4 | −286.2 |

Figure 5:
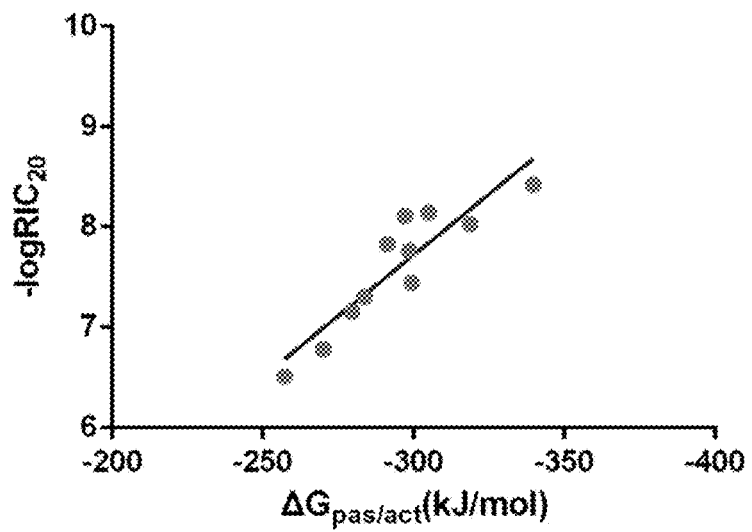
FIG. 5 depicts the regression plot of combined binding free energy with the anti-TH potencies.

As shown in FIG. 5, the antagonistic potency (−log RIC$_{20}$) of HO-PBDEs was well correlated with the combined binding free energy (ΔG$_{pas/act}$). The prediction model obtained using the training set in this example is given (Equation 2).

$$-\log RIC_{20} = 0.4115 - 0.0244 \Delta G_{pas/act} \quad (2)$$

The determination coefficient R$^2$=0.826, and the external explained variance Q$^2_{ext}$=0.926. The results indicated that the prediction model had good predictive ability. This prediction model can be utilized to predict the relative anti-TH potencies of potential TR antagonists, especially among HO-PBDEs, after qualitative identification following the procedure above.

The invention claimed is:

1. A screening method for thyroid hormone disruptors based on co-regulator involved simulations, comprising:
   1) constructing apo conformations of thyroid hormone (TH) receptor (TR) ligand binding domain (LBD) by using a reported protein crystal in a protein database as templates;
   2) for a training set of ligands:
      a) building ligand structures; docking the ligand structures into the TRs to form ligand-TR complexes; performing Molecular dynamics (MD) simulations for the ligand-TR complexes;
      b) obtaining equilibrated conformations of the ligand-TR complexes from the MD trajectories by extracting conformations when root-mean-square deviation of helix-12 (H12) of the TR is equilibrated or when H12 is in an average position of a fluctuation; identifying the ligands as passive antagonists if the ligands induce H12 to block a coactivator binding site;
      c) docking each of coactivator and corepressor to the equilibrated conformations obtained in step b) whose co-regulator binding sites are not blocked and thus be exposed to co-regulators; identifying the ligands as agonists if the docking scores of the equilibrated conformations for the corepressors are greater than the docking scores for the coactivators; identifying the ligands as active antagonists if the docking scores of the equilibrated conformations for the coactivators are greater than the docking scores for the corepressors;
      d) for those identified as agonists in step c), performing MD simulations again for the obtained ligand-TR-coactivator complexes; for those identified as active antagonists in step c), performing MD simulations again for the obtained ligand-TR-corepressor complexes;
      e) performing bioassays to obtain disrupting potencies of the ligands in the training set;
      f) calculating binding free energy between the TR and the passive antagonists using the MD simulations for the ligand-TR complexes performed in step a); calculating binding free energy between the TR and the active antagonists using the MD simulations for the ligand-TR-corepressor complexes performed in step d); calculating binding free energy between the TR and the agonists using the MD simulations for the ligand-TR-coactivator complexes performed in step d);
      g) building a passive antagonistic potency prediction model by regression analysis between the disrupting potencies obtained in step e) and the binding free energy between the TR and the passive antagonists; building an active antagonistic potency prediction model by regression analysis between the disrupting potencies obtained in step e) and the binding free energy between the TR and the active antagonists; building an agonistic potency prediction model by regression analysis between the disrupting potencies obtained in step e) and the binding free energy between the TR and the agonists;
   3) repeating steps 2a) to 2d) for one or more ligands of interest as steps 3a) to 3d);
   4) if the one or more ligands of interest is identified as a passive antagonist in step 3b), calculating binding free energy between the TR and the one or more ligands of interest using the MD simulations for the ligand-TR complexes performed in step 3a); if the one or more ligands of interest is identified as an active antagonist in step 3c), calculating binding free energy between the TR and the one or more ligands of interest using the MD simulations for the ligand-TR-corepressor complexes performed in step 3d); if the one or more ligands of interest is identified as an agonist in step 3c), calculating binding free energy between the TR and the one or more ligands of interest using the MD simulations for the ligand-TR-coactivator complexes performed in step 3d); and
   5) if the one or more ligands of interest is identified as the passive antagonist in step 3b), obtaining a TH passive antagonistic potency of the one or more ligands of interest by comparing the binding free energy between the TR and the one or more ligands of interest against the passive antagonistic potency prediction model; if the one or more ligands of interest is identified as the active antagonist in step 3c), obtaining a TH active antagonistic potency of the one or more ligands of interest by comparing the binding free energy between the TR and the one or more ligands of interest against the active antagonistic potency prediction model; if the one or more ligands of interest is identified as the agonist in step 3c), obtaining a TH agonistic potency of the one or more ligands of interest by comparing the binding free energy between the TR and the one or more ligands of interest against the agonistic potency prediction model.

2. The method of claim 1, wherein the constructing the apo conformations in step 1) is based on homology modeling and comprises constructing a loop between H11 and H12 according to a protein having PDB code 1A52 in the protein database as a template; and constructing the rest part of the apo conformations based on the reported crystal structures of TRs in the protein database.

3. The method of claim 1, wherein at least one of step 2a) and step 3a) further comprises optimizing the ligand structures built in step 2a) or step 3a) by performing MM2 (Molecular Mechanics, Allinger Force Field version 2), and then performing Powell gradient algorithm with the Tripos force field.

4. The method of claim 1, wherein the MD simulations of ligand-TR complexes in at least one of step 2a) and step 3a) are performed following the protocol: CHARMM force fields are applied to the receptors and ligands, respectively; each complex is immersed with TIP3P water molecules in a box, keeping the minimum distance between the complex and the boundary larger than 1.4 nm; Na+ and Cl− ions are added to neutralize the system; all MD simulations are performed in the NPT (constant pressure and temperature) ensemble in 1 atm, 300 K, with periodic boundary conditions; electrostatic interactions are calculated with the particle mesh Ewald method, with van der Waals interactions cutoff of 1.0 nm; all simulations are performed for 20-22 ns using a 2 fs time step, and snapshots for analysis are saved every 2 ps.

5. The method of claim 1, wherein the MD simulations of ligand-TR-coactivator/corepressor complexes in at least one of step 2d) and step 3d) are performed following the protocol: CHARMM force fields are applied to the receptors with coactivator/corepressor and ligands, respectively; each complex is immersed with TIP3P water molecules in a box, keeping the minimum distance between the complex and the boundary larger than 1.4 nm; Na+ and Cl− ions are added to neutralize the system; all MD simulations are performed in the NPT (constant pressure and temperature) ensemble in 1 atm, 300 K, with periodic boundary conditions; electrostatic interactions are calculated with the particle mesh Ewald method, with van der Waals interactions cutoff of 1.0 nm; all simulations are performed for 20-22 ns using a 2 fs time step, and snapshots for analysis are saved every 2 ps.

6. The method of claim 1, wherein the identifying the ligands as passive antagonists in at least one of step 2b) and step 3b) comprises evaluating whether the ligands induce H12 to block the coactivator binding site according to the distance between H12 and key residues: for TRβ having UniProt code P10828, H12 is considered blocking coactivator binding site if a distance between H12 and V284 and a distance between H12 and K306 are less than 3 Å, respectively, and a distance between H12 and K288 and a distance between H12 and I302 are less than 5 Å, respectively; for TRα having UniProt code P10827, H12 is considered blocking coactivator binding site if a distance between H12 and V230 and a distance between H12 and K252 are less than 3 Å, respectively, and a distance between H12 and K234 and a distance between H12 and I248 are less than 5 Å, respectively.

7. The method of claim 1, wherein the calculating the binding free energy in at least one of step 2f) and step 4) is based on MM-PBSA (molecular mechanics Poisson-Boltzmann surface area) method.

8. The method of claim 1, wherein the binding free energy between the TR and the passive antagonists are calculated by use of MD trajectories of passive antagonist-TR complexes; the binding free energy between the TR and the active antagonists is calculated by use of MD trajectories of active antagonist-TR-corepressor.

9. The method of claim 1, wherein the identifying the ligands as passive antagonists in at least one of step 2b) and step 3b) comprises evaluating whether the ligands induce H12 to block the coactivator binding site according to the distance between H12 and key residues: for TRβ having PDB code 1NQ0, H12 is considered blocking coactivator binding site if a distance between H12 and V284 and a distance between H12 and K306 are less than 3 Å, respectively, and a distance between H12 and K288 and a distance between H12 and I302 are less than 5 Å, respectively; for TRα having PDB code 4LNX, H12 is considered blocking coactivator binding site if a distance between H12 and V230 and a distance between H12 and K252 are less than 3 Å, respectively, and a distance between H12 and K234 and a distance between H12 and I248 are less than 5 Å, respectively.

10. The method of claim 1, wherein:
step f) further comprises obtaining a combined binding free energy by combining the binding free energy between the TR and the passive antagonists and the binding free energy between the TR and the active antagonists, and
step g) further comprises building an antagonistic potency prediction model by regression analysis between the disrupting potencies obtained in step 2e) and the combined binding free energy.

11. A screening method for thyroid hormone disruptors based on co-regulator involved simulations, comprising:
1) constructing apo conformations of thyroid hormone (TH) receptor (TR) ligand binding domain (LBD) by using a reported protein crystal in a protein database as templates;
2) for a training set of ligands:
   a) building ligand structures; docking the ligand structures into the TRs to form ligand-TR complexes; performing Molecular dynamics (MD) simulations for the ligand-TR complexes;
   b) obtaining equilibrated conformations of the ligand-TR complexes from the MD trajectories by extracting conformations when root-mean-square deviation of helix-12 (H12) of the TR is equilibrated or when H12 is in an average position of a fluctuation; identifying the ligands as passive antagonists if the ligands induce H12 to block a coactivator binding site;
   c) docking each of coactivator and corepressor to the equilibrated conformations obtained in step b) whose co-regulator binding sites are not blocked and thus be exposed to co-regulators; identifying the ligands as agonists if the docking scores of the equilibrated conformations for the corepressors are greater than the docking scores for the coactivators; identifying the ligands as active antagonists if the docking scores of the equilibrated conformations for the coactivators are greater than the docking scores for the corepressors;
   d) for those identified as active antagonists in step c), performing MD simulations again for the obtained ligand-TR-corepressor complexes;
   e) performing bioassays to obtain disrupting potencies of the ligands in the training set;

f) calculating binding free energy between the TR and the passive antagonists using the MD simulations for the ligand-TR complexes performed in step a); calculating binding free energy between the TR and the active antagonists using the MD simulations for the ligand-TR-corepressor complexes performed in step d);

g) building a passive antagonistic potency prediction model by regression analysis between the disrupting potencies obtained in step e) and the binding free energy between the TR and the passive antagonists; building an active antagonistic potency prediction model by regression analysis between the disrupting potencies obtained in step e) and the binding free energy between the TR and the active antagonists;

3) repeating steps 2a) to 2d) for one or more ligands of interest as steps 3a) to 3d);

4) if the one or more ligands of interest is identified as a passive antagonist in step 3b), calculating binding free energy between the TR and the one or more ligands of interest using the MD simulations for the ligand-TR complexes performed in step 3a); if the one or more ligands of interest is identified as an active antagonist in step 3c), calculating binding free energy between the TR and the one or more ligands of interest using the MD simulations for the ligand-TR-corepressor complexes performed in step 3d); and 5) if the one or more ligands of interest is identified as the passive antagonist in step 3b), obtaining a TH passive antagonistic potency of the one or more ligands of interest by comparing the binding free energy between the TR and the one or more ligands of interest against the passive antagonistic potency prediction model; if the one or more ligands of interest is identified as the active antagonist in step 3c), obtaining a TH active antagonistic potency of the one or more ligands of interest by comparing the binding free energy between the TR and the one or more ligands of interest against the active antagonistic potency prediction model.

12. The method of claim 11, wherein step f) further comprises obtaining a combined binding free energy by combining the binding free energy between the TR and the passive antagonists and the binding free energy between the TR and the active antagonists, and step g) further comprises building an antagonistic potency prediction model by regression analysis between the disrupting potencies obtained in step 2e) and the combined binding free energy.

* * * * *